United States Patent [19]

Nakao

[11] Patent Number: 5,782,840
[45] Date of Patent: Jul. 21, 1998

[54] SNARE CAUTERIZATION SURGICAL INSTRUMENT ASSEMBLY AND METHOD OF MANUFACTURE

[75] Inventor: Naomi L. Nakao, New York, N.Y.

[73] Assignee: Wilk & Nakao Medical Technology, Inc., New York, N.Y.

[21] Appl. No.: 800,607

[22] Filed: Feb. 14, 1997

[51] Int. Cl.[6] .................................................. A61B 17/24
[52] U.S. Cl. .......................... 606/114; 606/110; 606/113
[58] Field of Search .............................. 606/1, 106, 110, 606/114, 113, 127, 128, 151, 32, 37, 39, 40, 45–52

[56] References Cited

U.S. PATENT DOCUMENTS

5,192,286  3/1993  Phan et al. ........................ 606/127
5,279,539  1/1994  Bohan et al. ...................... 606/113
5,336,227  8/1994  Nakao et al. ...................... 606/113

*Primary Examiner*—Glenn K. Dawson
*Attorney, Agent, or Firm*—Abelman, Frayne & Schwab

[57] ABSTRACT

An improved snare cauterization instrument assembly is provided with a plurality of fixed connecting strands that severably join the web member to the cauterization loop to prevent the undesired movement of the web to the distal end of the loop prior to electrical activation and severing of the tissue sample. A method of manufacturing the assembly employs a resilient, flexible catheter as a tool to facilitate the placement of the web member on the loop.

20 Claims, 9 Drawing Sheets

SNARE CAUTERIZATION SURGICAL INSTRUMENT ASSEMBLY AND METHOD OF MANUFACTURE

FIELD OF THE INVENTION

This invention relates to an improvement in a surgical instrument assembly for use in snare cauterization operations.

BACKGROUND OF THE INVENTION

It is known from the disclosure of U.S. Pat. No. 5,486,182 issued to Nakao and Wilk to separably attach a flexible web member that forms a capture pocket to a conductive cauterization loop. The assembled web and cauterization loop are adapted to pass through a hollow sheath, which sheath and assembly form part of an endoscopic instrument for use in snare cauterization operations. The disclosure of U.S. Pat. No. 5,486,182 is incorporated herein in its entirety by reference.

As further disclosed in U.S. Pat. No. 5,486,182 a preferred means for separably joining the flexible web member, which can be a nylon mesh or net material, to the cauterization loop is by a plurality of nylon filaments or ringlets. These nylon filaments or ringlets are melted when electrical power is transmitted to the cauterization loop, thereby releasing the web which has been formed into a pouch or capture pocket.

What I have found in using an instrument assembly in accordance with the '182 patent is that when the cauterization loop was withdrawn into the sheath to close the loop around the polyp or other tissue to be severed, the strands of material connecting the web to the loop and, in some instances, the material comprising the web, moved along the loop and became concentrated at the distal end of the loop. The web material was bunched together and could become interposed between the polyp and the heated distal end of the cauterization loop. The presence of numerous filaments or ringlets by which the web was slidably joined to the loop also interfered with, and made more difficult and time-consuming the transection of the tissue. An additional problem encountered was the generation of excessive smoke from the burning of the nylon strands which impaired visibility through the endoscopic optical system.

It has also been found that the manufacture of snare cauterization instrument assemblies is time-consuming because of the difficulty of passing the connecting strands over the conduction wire cauterization loop. This is particularly so where a purse string is employed which itself must be woven through the web member.

It is therefore an object of this invention to provide an improved assembly for use in snare cauterization operations in which the flexible web forming the capture pocket does not become interposed between the tissue to be severed and the heated distal end of the cauterization loop.

It is another objective of the invention to provide means for severably attaching the flexible web to the cauterization loop so that the filaments or strands joining the web to the proximal ends of the loop are limited in their movement toward the distal end of the loop when the loop is closed around the tissue to be severed.

It is yet another object of the invention to provide means for severably securing the web of a snare cauterization assembly to the cauterization loop so that the movement of the web in the direction of the distal end of the loop is limited.

Another object of the invention is to provide means for attaching the flexible web of a snare cauterization assembly to the cauterization loop that will permit the web to be separated from the loop only at the distal end of the loop, the proximal portion of the web remaining attached to the loop in order to contain the severed tissue sample in the capture pocket of the web.

It is another object of the invention to provide an improved method for manufacture of snare cauterization instrument assemblies that is easier, faster and therefore less expensive than the prior art methods.

These and other objects of the invention will be apparent to those of ordinary skill in the art from the description which follows.

SUMMARY OF THE INVENTION

The improved instrument of the invention is intended for use in the cauterization and collection of tissues, (e.g. polyps) that are located in patients during endoscopic procedures. A snare comprising a flexible web member is placed over the tissue to be removed. The periphery of the web member is attached by a plurality of sliding connecting strands to the electrically conductive cauterization loop. Another group of at least three thermoplastic connecting strands are secured to the distal section of the loop at fixed positions. When an electric current is applied to the loop to sever and cauterize the tissue, the distal end section of the loop is raised to a cauterization temperature which is sufficient to cut through the tissue and seal the site to substantially prevent bleeding. The most distally attached thermoplastic connecting strands are melted by the heat generated in the distal end of the loop. Simultaneously, as the loop is closed, the desired tissue specimen is severed and the remaining stump of internal tissue is cauterized by the heat resulting from the current passing through the loop. As the proximal end of the loop is withdrawn into a sheath in the endoscope channel, the remaining sliding connecting strands attached to the web member are moved to the distal end of the loop, where the tissue sample is retained in the capture pocket of the web member. The specimen remains in the capture pocket of the web member, external to the endoscope tube during its removal from the body. When the loop is again advanced distally from the tip of the endoscope, the loop opens to thereby allow the specimen to be removed from the web member. Alternatively, the web member can be severed from the distal end of the loop after the assembly is removed from the patient.

A flexible web member that is formed from a net or mesh material and that is partially severably from a cauterization loop is secured in position on the cauterization loop of a snare cauterization assembly at a plurality of spaced apart locations on the distal end of the loop. By securing the web at a plurality of fixed positions, preferably at fixed positions located at about one-third to one-quarter of the distance from the distal end of the loop, that part of the web which is proximally displaced from the fixed attachment points cannot move past the fixed points towards the distal end of the loop.

In a preferred embodiment of the invention, the flexible web is secured at three spaced-apart locations that are past the midpoint of the loop toward the distal end of the loop. In a further preferred embodiment, the flexible web is secured at a first position at the extreme distal end or tip of the loop and at two or more additional positions that are spaced at approximately equal distances from the first position on the opposing arms forming the loop.

The web can be severably joined directly to the loop at a plurality of positions by strands that form a part of the web, or the web can be joined by means of intermediate filaments or strands, each of which filaments or strands are secured at one end to the loop and at the other end to the web, and preferably to the periphery of the web.

If the web further comprises a purse string to facilitate the closing of the mouth of the web to form the capture pocket, the connecting filaments or strands can be secured to the purse string since the purse string passes through and engages the periphery of the web throughout the distal section of the web. It will be understood that even though the plurality of the filaments which are fixed at one end to the distal end of the loop and at their other end to the purse string function to restrict distal movement of the web, they are not directly joined to the web material.

However, in a preferred embodiment of the improved snare cauterization assembly, the purse string is eliminated entirely. The elimination of the purse string greatly simplifies the manufacture of the assembly and therefore also reduces the labor and related costs. Since only the portion of the web at the -distal end of the loop is severed from the loop, the tissue sample is readily retained in the pocket formed by that portion of the web that remains joined to the loop. As will be appreciated by one familiar with the art, the severed tissue sample is sticky and once contacted by the web capture pocket will not be dislodged after the loop is closed and while the endoscope is withdrawn from the body.

As used herein, "web connecting strand" means both a strand that forms an integral part of the web that is in contact with the loop, or a separate strand that extends between the web and the loop, or between a purse string threaded through the web and the loop.

The means for severably securing the web connecting strands to the cauterization loop can be mechanical, as by the use of clamps, apertures or grooves in the loop, and the like. Combinations of such mechanical means can also be used to secure the connecting strands. Alternatively, the web connecting strands can be severably secured to the loop at a plurality of positions using self-bonding adhesive material or a separate adhesive material. As used herein, the term "self-bonding adhesive" is defined to mean a material or method that can be altered, as by the application of heat or a solvent to become sufficiently tacky that it will form a bond with the surface of the cauterization loop. Polymeric materials, when heated to a temperature less than their decomposition or ignition temperatures become thermoplastic with sufficient tackiness, or adhesive properties, to bond to a dissimilar surface such as metal. Numerous compositions that have been developed for commercial use as hot-melt adhesives can be employed.

When the web has been severably joined to the loop at a plurality of fixed positions at the distal section of the loop, the connecting strands at the proximal end of web will not be able to slide distally past the fixed positions that are closest to the proximal end of the loop. The movement of the connecting strands at the distal end of the web will also be limited so that the capture pocket can be more easily maneuvered into proper position over the polyp that is to be transected. For example, if the web is secured so that one-quarter of the periphery of the web at the distal end of the loop restrained from sliding, the remaining three-quarters of the web can move distally.

By fixing the distal section of the web with respect to the loop, there is also avoided the tendency of the web to bunch up in one position on the loop in the event that it becomes necessary to completely retract the assembly into the hollow sheath in order to reposition the endoscope in the patient. Likewise, the movement or repositioning of the extended loop and web during a procedure is greatly facilitated.

When the loop and web are deployed at the surgical site of the transection, for example, of a polyp, the proximal end of the loop is withdrawn to tighten the distal end of the loop about the stem of the polyp. Since the connecting strands of the web are severably secured to the distal end of the loop at a plurality of positions, the movement of the proximal end of the web member toward the distal end of the loop is limited and neither the web nor connecting strands can become interposed between the distal end of the loop and the tissue to interfere with the procedure.

When the electrical current is transmitted through the loop to sever and cauterize the tissue, the means by which the web is secured at fixed positions to the loop are also severed, i.e., melted by the heat generated in the loop. However, because the material of the connecting strands joining the web to the loop either directly or indirectly constitutes a relatively small volume, and it is melted quickly, the fumes generated are minimal and do not interfere with the visualization of the surgical site via the optical system in the endoscope.

Because of the sticky nature of the bodily fluids on the surface of the tissue sample, the sample remains in contact with the inner surface of the web capture pocket and will not fall out of the pocket during egress of the endoscope from the body.

In accordance with a further embodiment of the invention, an improved method of manufacturing the assembly of the invention is provided. As will be known to those familiar with the art, the cauterization loop is disposable, and is a preformed wire loop having two free ends that are inserted into a connector. The improved manufacturing method of the invention comprises the steps of (a) inserting a flexible catheter through the connecting strands that are attached to, or which form the periphery of the web; (b) passing one free end of the preformed cauterization loop through the annular passageway of the catheter; (c) positioning the connecting strands of the web on the catheter so that they do not extend beyond the free ends of loop; (d) removing the catheter from the loop and the connecting strands, while simultaneously holding the connecting strands and web in a fixed position with respect to the loop; (e) securing at least three spaced-apart connecting strands to the loop at positions proximate the distal end of the loop.

The catheter used in the improved method is sufficiently flexible to follow the contour of the preformed conductive metal wire loop and strong enough to resist puncturing by the free end of the curve loop. The exterior surface of the catheter is smooth with a low coefficient of friction to facilitate sliding contact with the connecting strands of the web. The catheter can be made of a tetrafluoretheylene fluorocarbon polymer, such as TEFLON®, or other polymers and copolymers having similar properties. Suitable catheters are commercially available.

Figure 1A:
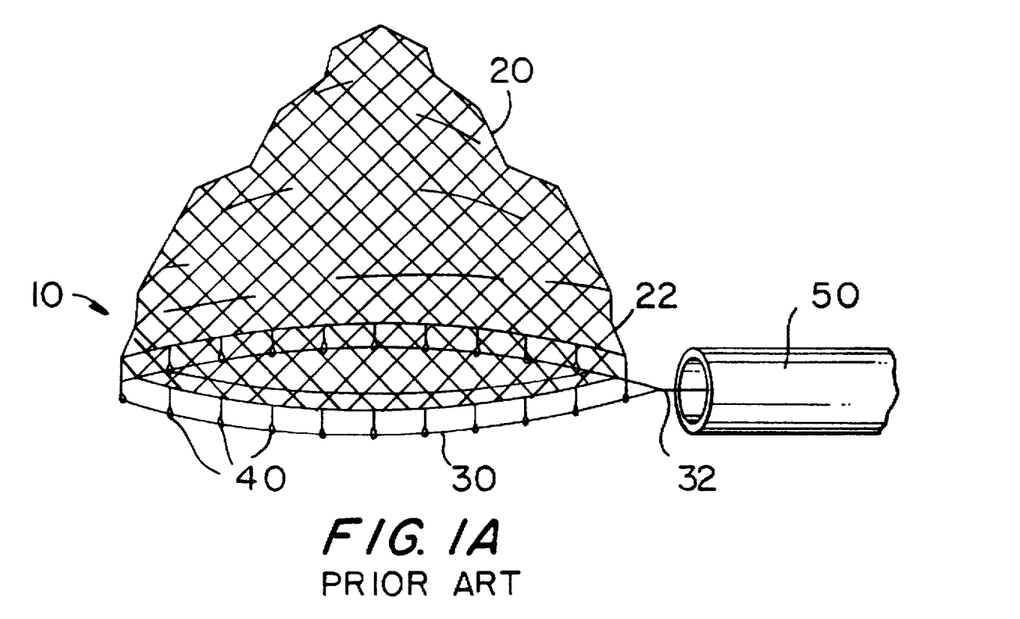
FIG. 1A and FIG. 1B are schematic partial side perspective views showing two embodiments of a snare cauterization instrument assembly of the prior art.
Figure 1B:
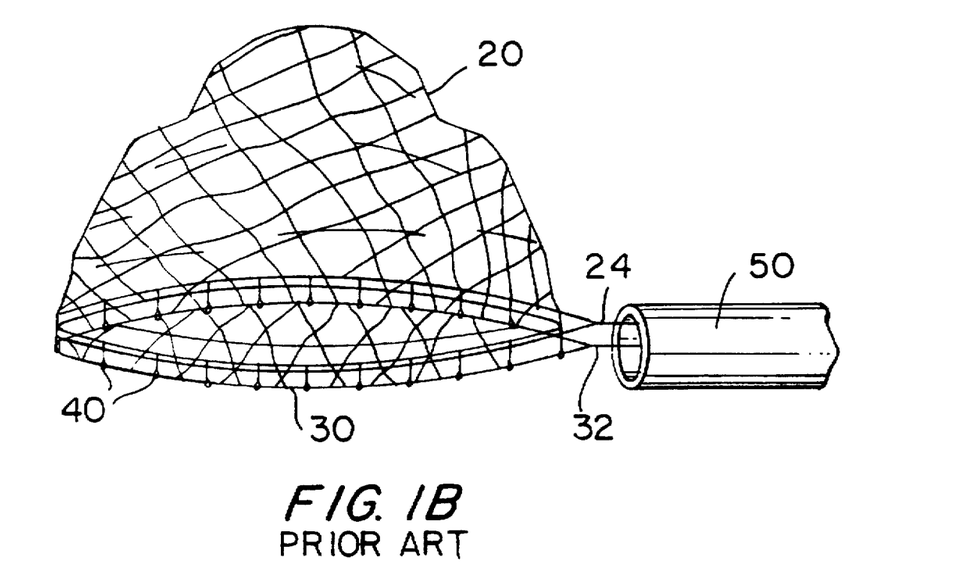
Figure 2:
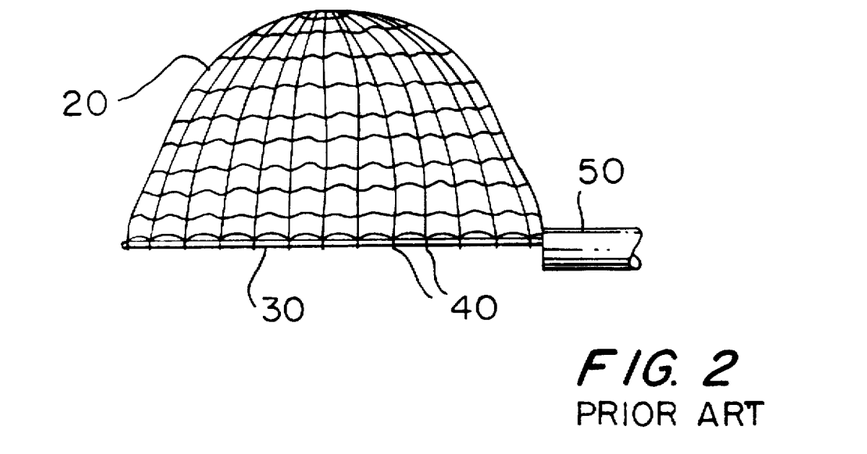
FIG. 2 is a schematic side elevational view, on an enlarged scale, of another embodiment of a snare cauterization instrument assembly, showing a pocket-defining web member on a loop of the prior art.

In the description of the figures which follow, like structural components bear the same reference designations. FIG. 1A and 1B show a capture web 20 in the form of a net fastened to loop 30. Capture web 20 is thin and flexible and preferably made of biologically inert flexible transparent synthetic resin or polymeric material such as polyethylene or nylon. Prior to the beginning of a snare cauterization operation, web 20 is disposed in a closed, folded or contracted state, together with loop 30, in the distal end of tubular member 50.

The web 20 is attached to loop 30 along web periphery 22 by a plurality of sliding connecting strands 40 that pass around loop 30 and are tied or otherwise connected at their opposite ends to the periphery 22 of web member 20.

Figure 3A:
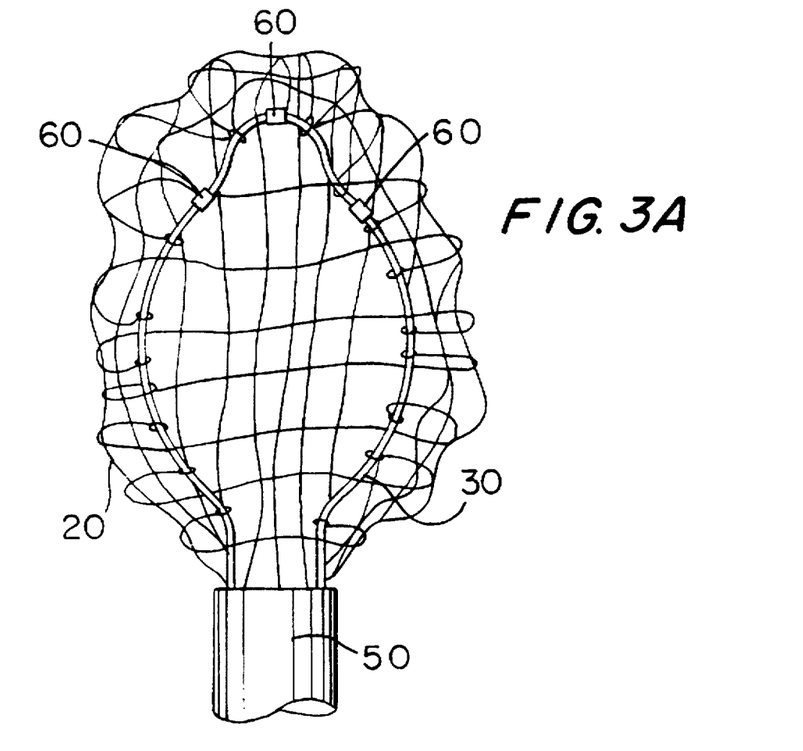
FIG. 3A is a schematic perspective view, also on an enlarged scale, of a modified snare cauterization instrument assembly, showing an auxiliary loop attached at three points to a cauterization loop.

FIG. 3A. shows a cauterization loop 30 with web member 20 joined at three fixed positions by clamps 60 that secure three connecting strands 42 to a distal end of the loop. This permanent attachment of the sliding connecting strands at the proximal end of the web 20 to the loop 30 can be in the form of a ringlet, a wound thread that is tied or joined at its free end by a spot of adhesive, etc. Permanent attachment of the proximal sliding connecting strands 40 through the loop 30 prevents separation of capture and pocket 20 from loop 30 during the transection procedure and provides additional assurance that the capture pocket will not become detached from loop 30 while inside the patient.

Figure 3B:
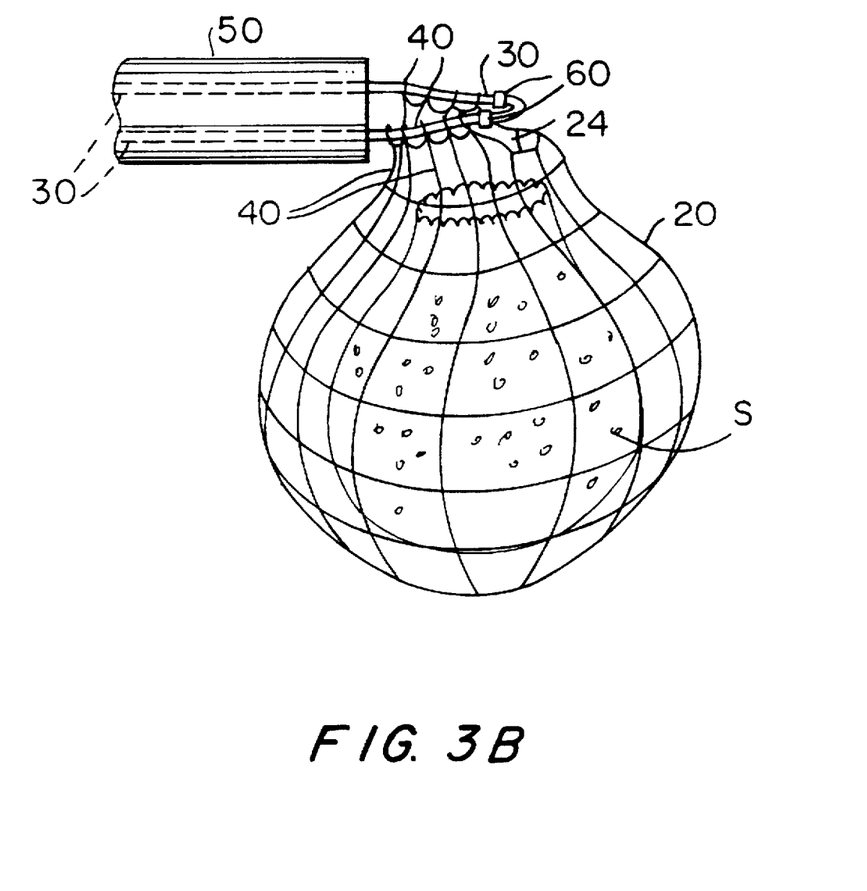
FIG. 3B is a schematic perspective view of the instrument assembly of FIG. 3A following a surgical procedure for recovery of a tissue sample.

As shown in FIG. 3B, after the electrical current is supplied to the loop to sever the tissue sample, the severed tissue sample S is contained in the web capture pocket 20. When the loop 30 is withdrawn into tubular member 50, the sliding connecting strands 40 previously located at the proximal end of the loop are moved toward the distal end of the loop. The fixed connecting strands 42 (and any intervening sliding strands 40) have been melted by the cauterization heat and only the three clamps 60 remain affixed to the loop at its distal end portion. An opening 24 in the web exists where the fixed and any intervening sliding connecting strands were melted. However, because of the relatively small size of the unattached portion of the web periphery and its tacky or sticky surface, the sample S will not become dislodged from its position inside the capture pocket.

Figure 4:
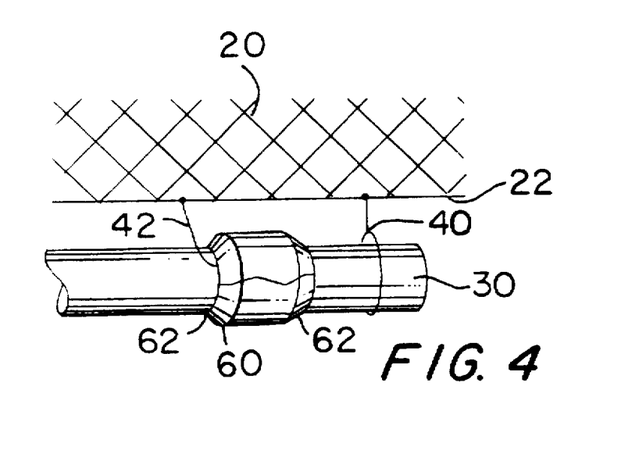
FIG. 4 is a schematic perspective view of portion of a loop illustrating one means for clamping a web connecting strand at a fixed position.

As better shown in the enlarged view of FIG. 4, clamp 60 secures connecting strand 42 to a fixed position on loop 30. In the embodiment shown, clamp 40 is a slip annular ring having an inside diameter when compressed that is approximately the same as the outer diameter of loop 30 which has a circular cross-section. The free end of connecting strand 42 is maintained in position by being compressed between the clamp and surface of loop 30. In the preferred embodiment shown, clamp 60 has beveled edges so that the clamp will not engage or damage tissue with which it may come in contact. Also shown in FIG. 4 adjacent to clamp 60 is a sliding connecting strand that has been passed around the loop 30 and its free end tied or otherwise joined so that it can move in sliding contact with the loop. However, the presence of the fixed connecting strand 42 precludes the further movement of sliding connecting strands 40 in either direction along the loop 30. Thus, that portion of the web which is proximal to the rear-most fixed connecting strand 42 on each of the opposing arms of the loop 30 cannot move distally beyond the fixed strand. By this means, the distal end of the loop 30 is kept free of an accumulation of web material and/or connecting strands that might otherwise interfere with the severing and cauterization of the tissue sample.

The fixing of at least three connecting strands at the distal end of the loop 30 also serves the beneficial purpose of maintaining the proper configuration of the distal end of the web member 20 during movement and positioning of the loop over the tissue sample. While the number of fixed connecting strands to be secured and their precise position is not critical, it is preferred that at least three strands be so fixed, as by clamp members or other means described below, and that the number of sliding strands intermediate the fixed strands be kept to a minimum. In a preferred embodiment, the number of sliding connecting strands lying between the fixed connecting strands at the distal end of the loop is less that 50% of the total number of sliding connecting strands employed to join the web to the loop 30. In a most preferred embodiment, the number of intermediate sliding connecting strands is no more that about 20% of the total number of sliding strands.

Figure 5:
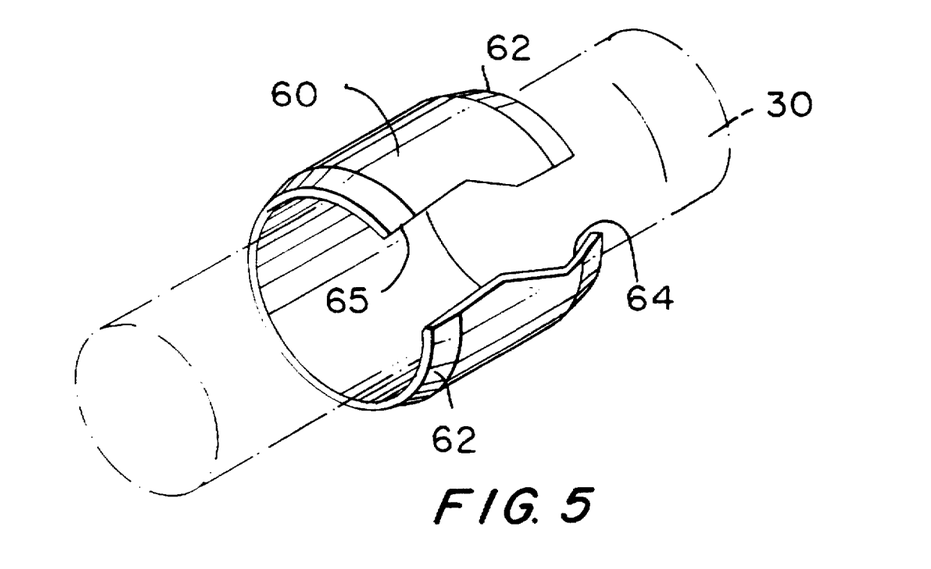
FIG. 5 is a perspective view of the clamp shown in FIG. 5 with the loop shown in phantom.

There is shown in FIG. 5 a further enlarged view of one embodiment of clamp 60 in its original expanded position prior to securing it to a fixed position on loop 30 (shown in phantom.) As will be understood by one of ordinary skill in the art, clamp 60 can be fabricated from a malleable metal, or metal alloy, so that the opening between split faces 64 and 65 permit the open clamp to be easily passed over the loop. After a connecting strand 42 has been placed between the clamp and surface of the loop, the clamp is compressed, most conveniently with a tool adapted for this purpose (not shown), until faces 64 and 65 are in touching alignment, or very close proximity. As noted previously, the beveled surfaces 62 are desirable to eliminate rough leading edges.

Figure 6A:
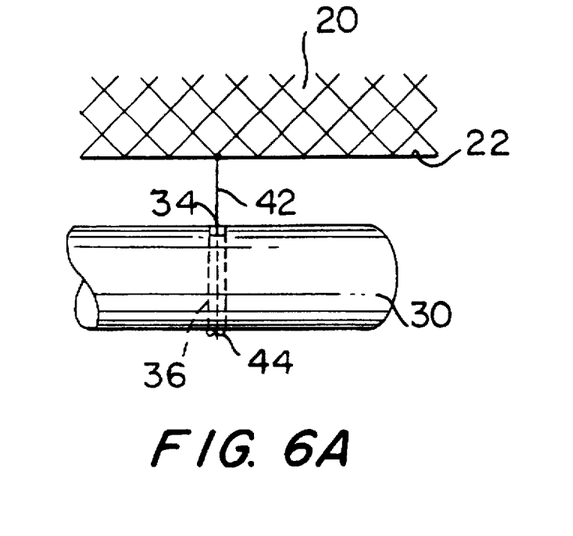
FIGS. 6A and 6B are perspective views showing other embodiments for practicing the method of the invention.

Shown in FIG. 6A is a alternative means for securing connecting strand 42 at a fixed position along the distal end of loop 30. An opening 34 leads to an orifice 36 which passes through loop 30. A connecting strand from the periphery 22 of web 20 passes through the orifice and is secured from movement as by means of a knot, adhesive, or the like at 44.

Figure 6B:
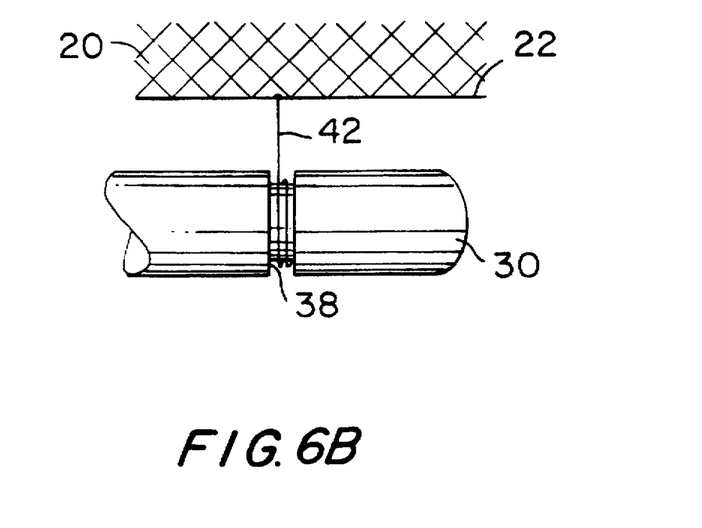

In the embodiment of FIG. 6B, loop 30 is provided with groove 38 into which the free end of connecting strand 42 is placed and wrapped one or more times and then tied or adhesively bound to secure the strand against movement. Other means will occur to those skilled in the art for securing the several connecting strands at fixed positions along the distal end of the loop 30.

It will also be understood by those of ordinary skill in the art that the cauterization loop is heated to a sufficient temperature to sever the tissue sample and cauterize the remaining surface at its distal end. Since the fixed points of attachment of the connecting strands must be severed by the heat generated, these positions must be fixed within the distal region reaching temperatures sufficient to melt the thermoplastic material from which the connecting strands are made. Commercially available cauterization loops or wires of the type useful in this invention typically reach elevated temperatures at the distal end over a distance which is from about one-quarter to about one-third of the overall length of the loop.

In preparation for use of the snare cauterization instrument assembly 10 of the invention as illustrated in FIGS. 1A–3, cauterization loop 30 is expanded from a collapsed configuration inside the distal end of sheath member 50 to the expanded configuration shown in the drawings.

Pursuant to additional steps in the procedure, capture pocket of web member 20 is opened during the expansion of cauterization loop 30 and the expanded loop is passed over a selected polyp or other internal tissue agglomeration to be removed, so that web member 20 substantially surrounds the polyp. Cauterization loop 30 is then closed by pulling it into the distal end of sheath member 50. The closure of cauterization loop 30 around a base region of the polyp while the cauterization loop is energized with electrical current serves to sever the polyp at its base. Maintaining web member 20 surrounding the polyp during the cauterization procedure serves to capture the severed polyp at the instant of its severance.

Loop 30 is further retracted into sheath member 50 upon the termination of a cauterization operation. Web member 20 and the captured internal body tissues remain outside of sheath member 50. As the loop 30 is retracted the sliding connecting strands are caused to move distally along the loop 30 by their contact with the leading edge of sheath member 50.

In preferred embodiment, the distal end of web 20 is initially connected to loop 30 by the at least three connecting strands in fixed positions and a minimal number of intermediate sliding connecting strands which are burned off or otherwise severed during a cauterization operation, thereby leaving the capture pocket of the web joined to loop 30 by the plurality of sliding connecting strands at the proximal end of the web.

In the practice of the method of this invention, the web which forms the capture pocket is prevented from moving along the opposing arms of the loop to accumulate at the distal end of the loop by securing several connecting strands at fixed positions proximate the distal end of the cauterization loop. Thus, the method contemplates recovering a selected portion of internal body tissues of a patient with an endoscopic surgical snare instrument, said instrument comprising an electrically conductive cauterization loop connected to a source of electrical energy and a flexible web member connected to said loop essentially around the circumference thereof by a plurality of sliding connecting strands that are in sliding contact with said loop and said web member further connected to said loop by at least three connecting strands at fixed positions along the distal end of said loop, said method comprises the steps of:

passing the loop over the selected internal body tissues to be removed so that the web member substantially surrounds said selected internal body tissues in the form of a capture pocket;

drawing the distal end of said loop into closing contact around a base region of said selected internal body tissues;

during said step of drawing and closing said loop, conducting an electrical current through said loop to sever said selected internal body tissues at said base region;

during said step of conducting an electrical current through said loop, melting and severing said at least three connecting strands at fixed positions and said sliding connecting strands intermediate said at least three connecting strands along the distal end of said loop;

withdrawing the closed loop and the web member containing the severed selected internal body tissues in the capture pocket from the surgical site; and sliding the unsevered connecting strands along the opposing sides of said loop toward the distal end of said loop to thereby dispose said web member at the distal end of said loop.

The improved method for manufacturing the snare cauterization assembly is schematically illustrated in FIGS. 7A–7D. As shown in 7A, a flexible catheter 70 having central orifice 72 is passed through the connecting strands 40 attached to the web. As previously described, it will be understood that the connecting strands 40 can be the same filaments or fibers that comprise the web, or connecting strands 40 can be separate elements that are joined to the periphery of the web, or to a purse string, in the event that one is used.

Figure 7A:
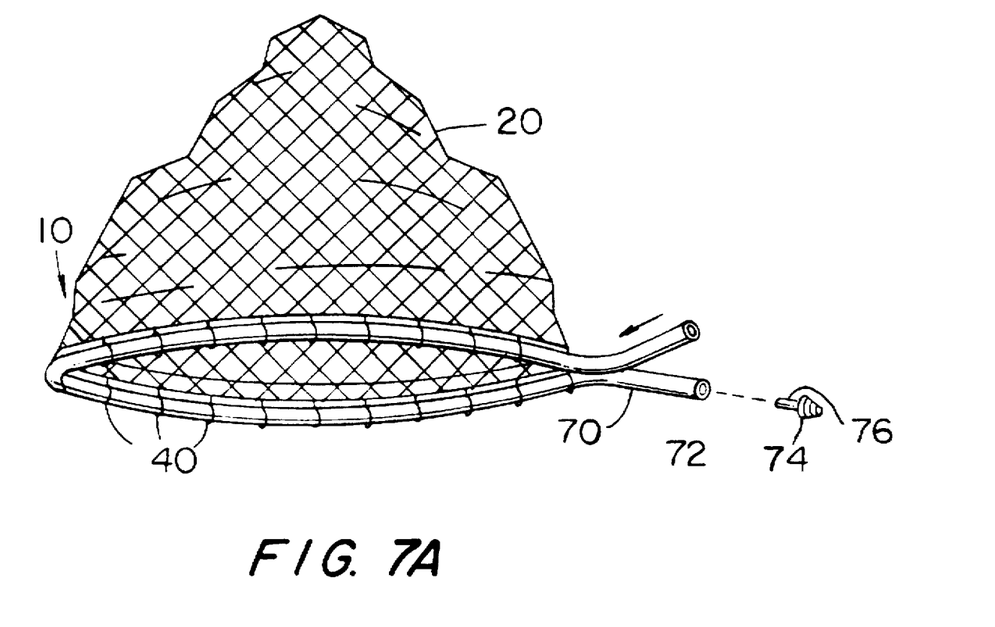
FIGS. 7A–D are schematic perspective views illustrating the improved method for manufacturing the snare cauterization assembly.

In a further preferred embodiment, a conical or rounded tip 74 having shaft 76 that is inserted in orifice 72 to facilitate the threading of the catheter through the web connecting strands. Alternatively, the end of the catheter that is to be threaded through the free ends of the connecting strands can be shaped, e.g., rounded, to facilitate its passage.

Figure 7B:
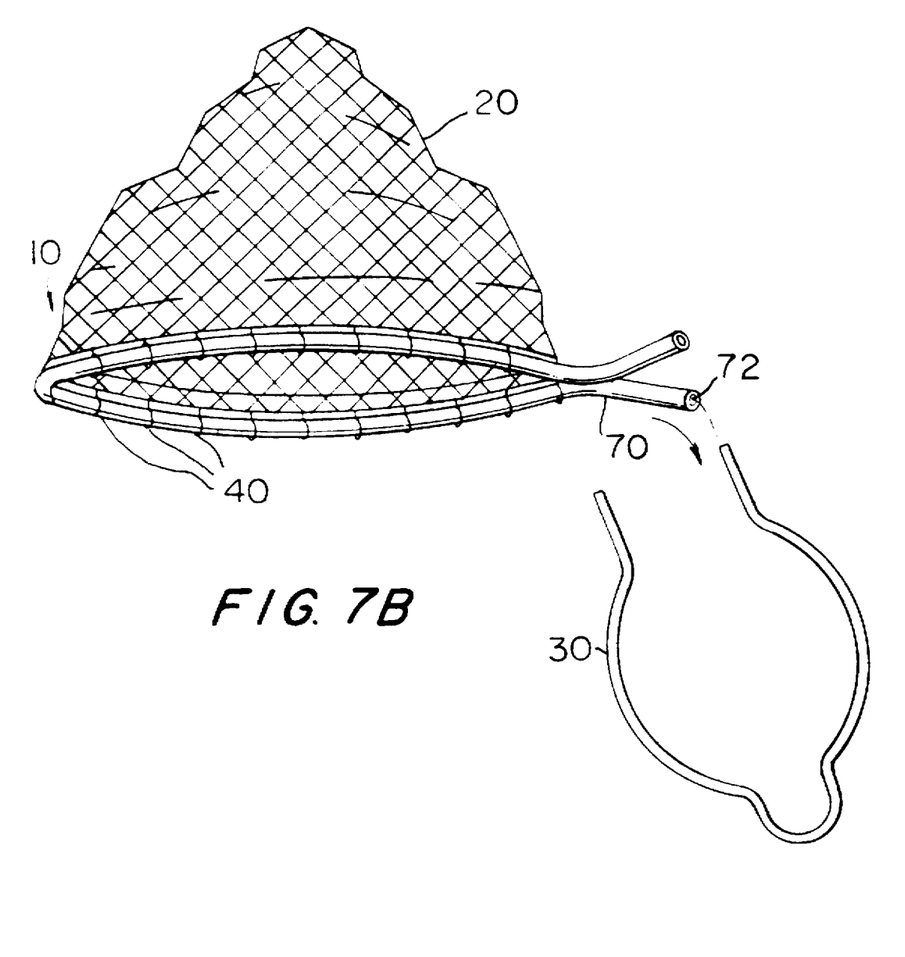
Figure 7C:
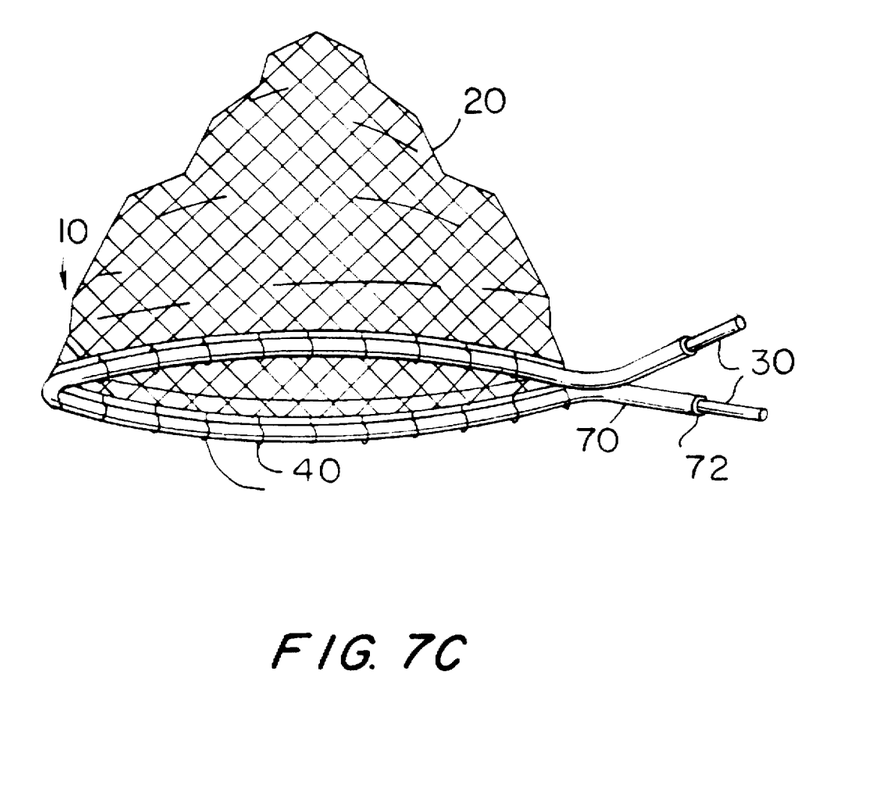
Figure 7D:
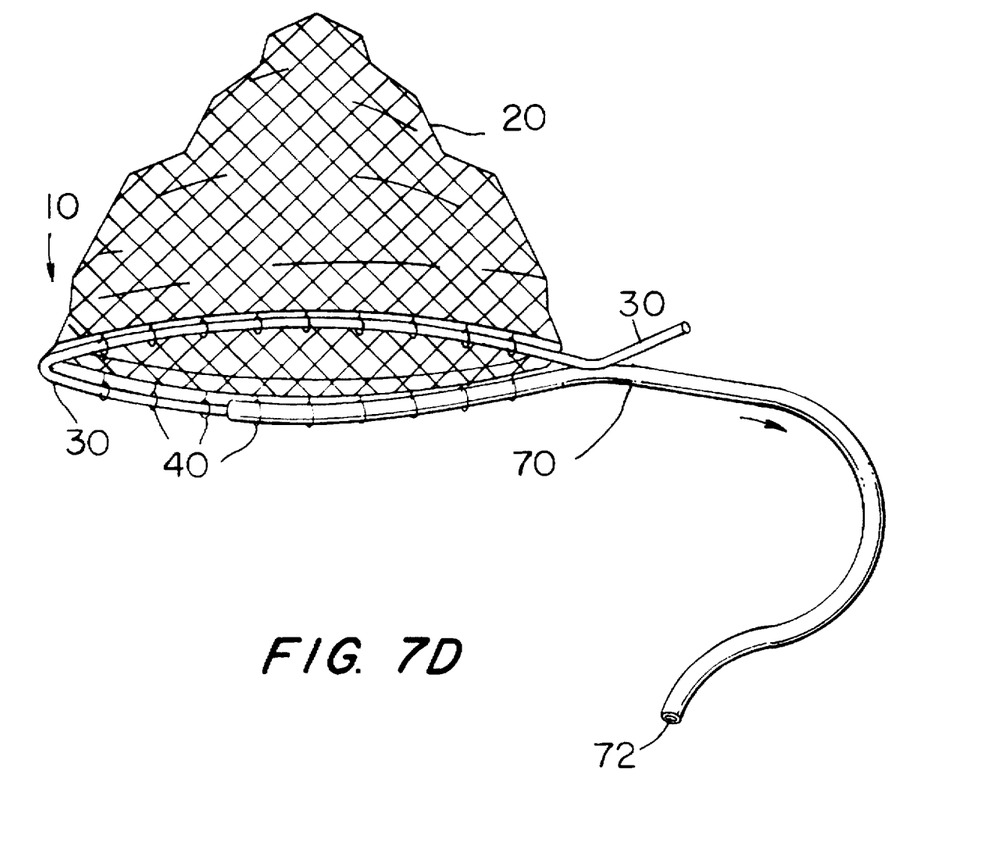

As shown in FIG. 7B, after the web is placed on the catheter, one of the free ends of the wire cauterization loop 30 is pushed into orifice 72 of catheter 70. The catheter and web are moved until they are positioned on the loop, as shown in FIG. 7C. Thereafter, as shown in FIG. 7D, the catheter 70 is removed from the loop 30 by pulling on one of the free ends of the catheter, while at the same time holding the web in a stationary position relative to the loop 30. Note in FIG. 7D the catheter 70 has been partially removed by sliding it off the loop. The catheter can be reused. The use of the catheter greatly reduces the time required for assembly, thereby reducing the labor and related cost.

Once the web 20 is in the desired position on the loop, a plurality of the connecting strands 40 can be severably secured to the distal end of loop 30 in accordance with the methods described above.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An improved endoscopic surgical snare cauterization instrument comprising an electrically conductive cauterization loop and a flexible web member, said loop having a cauterization section at its distal end, said web member forming a capture pocket having a mouth defined by said loop, said web member being joined to said loop by a plurality of sliding connecting strands of thermoplastic material, the improvement which comprises means for severably securing at least three connecting strands at fixed positions along the distal end of the cauterization loop.

2. The snare cauterization instrument of claim 1 where one of the at least three fixed connecting strands is at the distal tip of the loop and the positions of the other fixed connecting strands are spaced at approximately equal distances from the distal tip on the opposing arms of the loop.

3. The snare cauterization instrument of claim 1 where the at least three fixed connecting strands are at spaced apart positions along the cauterization section of the loop.

4. The snare cauterization instrument of claim 1 in which the at least three fixed connecting strands are at spaced-apart positions on the distal end of the loop that reaches cauterization temperature.

5. The snare cauterization instrument of claim 1 where the means for severably securing the connecting strands at the fixed positions is a clamp.

6. The instrument of claim 5 where the clamp is metal.

7. The instrument of claim 5 where the clamp contacts at least one connecting strand.

8. The instrument of claim 5 where the cross-section of the loop is circular and the clamp is annular with an inside diameter approximately equal to the diameter of the loop.

9. The instrument of claim 8 where the clamp has a longitudinal parting line and tapered edges, and the clamp is bent to conform to the surface of the loop and secure the clamp and at least one connecting strand to the loop.

10. The snare cauterization instrument of claim 1 where the means for severably securing each of the at least three connecting strands at fixed positions along said loop is a corresponding number of orifices in said loop through each of which orifices a connecting strand is passed and secured against movement.

11. The snare cauterization instrument of claim 1 where the means for severably securing each of the at least three connecting strands at a fixed position along said loop is a corresponding number of radial grooves in the surface of said loop, into each of which grooves is a connecting strand wrapped and secured against movement.

12. A method for recovering a selected portion of internal body tissues of a patient with an endoscopic surgical snare instrument, said instrument comprising an electrically conductive cauterization loop connected to a source of electrical energy and a flexible web member connected to said loop essentially around the circumference thereof by a plurality of sliding connecting strands that are in sliding contact with said loop and said web member is further connected to said loop by at least three fixed connecting strands at fixed positions along the distal end of said loop, said method comprising the steps of:

passing the loop over the selected internal body tissues to be removed so that the web member substantially surrounds said selected internal body tissues in the form of a capture pocket;

drawing the distal end of said loop into closing contact around a base region of said selected internal body tissues;

during said step of drawing and closing said loop, conducting an electrical current through said loop to sever said selected internal body tissues at said base region;

during said step of conducting an electrical current through said loop, melting and severing said at least three fixed connecting strands at fixed positions and any sliding connecting strands intermediate said at least three fixed connecting strands along the distal end of said loop;

withdrawing the loop and the severed selected internal body tissues contained in the capture pocket of the web member; and moving the unsevered sliding connecting strands along the opposing sides of said loop toward the distal end of said loop to thereby dispose said web member at the distal end of said loop.

13. The method of claim 12 where said melting and severing of said sliding connecting strands and said at least three fixed connecting strands occurs along about one-third the length of the loop as measured from the distal end of said loop.

14. The method of claim 12 where the number of sliding connecting strands lying between the at least three fixed connecting strands at fixed positions is less than half of the total number of sliding connecting strands that connect said web member to said loop.

15. The method of claim 12 where the number of sliding connecting strands lying between the at least three fixed connecting strands at fixed positions is less than 20% of the total number of sliding connecting strands that connect said web member to said loop.

16. A method for joining a flexible web member to an electrically conductive cauterization loop, where said web is connected to said loop by a plurality of sliding connecting strands of thermoplastic material that pass around said loop, the method comprising severably securing at least three connecting strands formed from thermoplastic material at fixed spaced apart positions along the cauterization section at the distal end of said loop.

17. The method of claim 16 where the securing of said at least three connecting strands is by engaging each of said at least three connecting strands with a clamp to thereby fix their respective positions along said loop.

18. An improved method for manufacturing a snare cauterization instrument assembly comprising a flexible web member in the form of a capture pocket joined to an electrically conductive cauterization loop by a plurality of sliding connecting strands, the method comprising the steps of (a) inserting a flexible-catheter through the connecting strands that are attached to, or which form the periphery of the web;

(b) passing one free end of the preformed cauterization loop through the annular passageway of the catheter;

(c) positioning the connecting strands of the web on the catheter so that they do not extend beyond the free ends of the loop;

(d) removing the catheter from the loop and the connecting strands, while simultaneously maintaining the connecting strands and web in a fixed position with respect to the loop;

(e) severably securing at least three spaced-apart connecting strands to the loop at positions proximate the distal end of the loop.

19. The method of claim 18 where the catheter is made from a resilient flexible polymer having a low coefficient of friction.

20. The method of claim 18 where the catheter is provided with a tip member to facilitate the passage of the free end of the catheter through the connecting strands.

* * * * *